United States Patent
Masciarelli et al.

(10) Patent No.: US 9,816,915 B2
(45) Date of Patent: Nov. 14, 2017

(54) COUPLINGS FOR FLAME OBSERVATION DEVICES

(71) Applicant: Fireye, Inc., Derry, NH (US)

(72) Inventors: David Masciarelli, Hooksett, NH (US); Thomas Corti, Hooksett, NH (US)

(73) Assignee: Fireye, Inc., Derry, NH (US)

( * ) Notice: Subject to any disclaimer, the term of this patent is extended or adjusted under 35 U.S.C. 154(b) by 310 days.

(21) Appl. No.: 14/508,513

(22) Filed: Oct. 7, 2014

(65) Prior Publication Data
US 2015/0104750 A1    Apr. 16, 2015

Related U.S. Application Data

(60) Provisional application No. 61/889,934, filed on Oct. 11, 2013.

(51) Int. Cl.
| | |
|---|---|
| *G01N 21/15* | (2006.01) |
| *F23M 11/04* | (2006.01) |
| *G01N 21/01* | (2006.01) |
| *G01N 21/72* | (2006.01) |
| G01D 11/26 | (2006.01) |
| G01J 1/04 | (2006.01) |

(52) U.S. Cl.
CPC .......... *G01N 21/01* (2013.01); *F23M 11/042* (2013.01); *G01N 21/72* (2013.01); *F23N 2900/05005* (2013.01)

(58) Field of Classification Search
CPC ...... G01N 21/01; G01N 21/72; F23M 11/042; F23N 2900/05005; F23N 2900/05004; G01D 11/26; G01J 1/0407; G01J 3/0205; G01J 5/0875

USPC ............................................ 431/13; 126/200
See application file for complete search history.

(56) References Cited

U.S. PATENT DOCUMENTS

| | | | | |
|---|---|---|---|---|
| 846,475 | A | * | 3/1907 | Hosking ................. C21B 7/163 126/200 |
| 911,579 | A | * | 2/1909 | Davis ...................... C21B 7/163 126/200 |
| 1,349,562 | A | * | 8/1920 | Curry ....................... F23M 7/00 110/173 R |
| 1,360,191 | A | * | 11/1920 | Datka ..................... C21B 7/163 126/200 |

(Continued)

FOREIGN PATENT DOCUMENTS

| | | | | |
|---|---|---|---|---|
| EP | 0299935 A1 | * | 1/1989 | ............... F24C 15/04 |
| JP | 08246127 A | * | 9/1996 | ............... C23C 16/52 |
| JP | 2004028982 A | * | 1/2004 | ............... G01N 21/01 |

*Primary Examiner* — Gregory Huson
*Assistant Examiner* — Daniel E Namay
(74) *Attorney, Agent, or Firm* — Locke Lord LLP; Scott D. Wofsy; Christopher J. Cillié

(57) ABSTRACT

A window for viewing combustion includes a window body having an interior surface facing a combustion space, an opposed exterior surface facing an instrument space, and a seal surface between the interior and exterior surfaces. The seal surface tapers from the interior surface to the exterior surface and hermetically separating the instrument space from the combustion space. A coupling for connecting a combustion space to an instrument space includes a union body, flanged body and locking body all aligned along an optical axis. The union body defines a tapered bore in which a viewing window for viewing combustion is disposed.

19 Claims, 6 Drawing Sheets

(56) References Cited

U.S. PATENT DOCUMENTS

| | | | | |
|---|---|---|---|---|
| 1,376,498 A * | 5/1921 | Zimmerman | F27D 21/02 | 126/200 |
| 1,376,550 A * | 5/1921 | Kelley | F27D 21/02 | 126/200 |
| 2,418,845 A * | 4/1947 | Long | F23N 5/085 | 250/205 |
| 3,021,386 A * | 2/1962 | Clark | G01J 5/02 | 126/200 |
| 3,110,274 A * | 11/1963 | Carey | F23M 11/042 | 110/179 |
| 3,145,705 A * | 8/1964 | Bruce | F23M 11/042 | 110/179 |
| 3,385,285 A * | 5/1968 | King | F23M 11/042 | 126/200 |
| 3,475,859 A * | 11/1969 | Pirlet | B01J 3/004 | 15/250.29 |
| 3,800,716 A * | 4/1974 | Berger | F23M 7/00 | 110/173 R |
| 3,859,041 A * | 1/1975 | Winslow | F27B 5/04 | 110/173 R |
| 3,936,196 A * | 2/1976 | Wickersheim | G01N 21/031 | 126/200 |
| 4,210,120 A * | 7/1980 | Ritopecki | F23M 11/042 | 126/200 |
| 4,277,131 A * | 7/1981 | Hart | F23M 11/042 | 356/439 |
| 4,322,627 A * | 3/1982 | Pirlet | C21B 7/24 | 250/236 |
| 4,432,286 A * | 2/1984 | Witte | F23N 5/082 | 110/185 |
| 4,455,996 A * | 6/1984 | Achilles, Sr. | F23J 13/00 | 126/200 |
| 4,612,908 A * | 9/1986 | Van Patten | F24B 1/191 | 126/200 |
| 4,800,278 A * | 1/1989 | Taniguti | G01J 5/34 | 250/338.1 |
| 4,833,303 A * | 5/1989 | Mellen, Sr. | F27D 19/00 | 110/180 |
| 4,840,474 A * | 6/1989 | Heft | G02B 23/2492 | 348/83 |
| 4,931,624 A * | 6/1990 | Mellen, Sr. | F27D 19/00 | 117/15 |
| 4,951,652 A * | 8/1990 | Ferrario | F24C 15/04 | 126/190 |
| 5,062,411 A * | 11/1991 | Karabin | F24B 1/1888 | 126/200 |
| 5,306,209 A * | 4/1994 | Lang | C21B 7/24 | 432/32 |
| 5,777,668 A | 7/1998 | Amano | | |
| 6,069,652 A * | 5/2000 | Eversole | H04N 5/2252 | 348/83 |
| 6,106,276 A * | 8/2000 | Sams | F23D 14/46 | 126/110 C |
| 6,108,072 A | 8/2000 | Lepain et al. | | |
| 6,278,374 B1 | 8/2001 | Ganeshan | | |
| 6,439,171 B1 * | 8/2002 | McCall | F23M 7/00 | 122/19.2 |
| 6,579,005 B2 | 6/2003 | Ingallinera | | |
| 6,652,266 B1 | 11/2003 | Murgu et al. | | |
| 6,694,683 B2 * | 2/2004 | Anderson | F23M 11/042 | 40/651 |
| 6,734,463 B2 * | 5/2004 | Ishikawa | H01L 29/78633 | 257/434 |
| 7,240,673 B2 * | 7/2007 | Class | F23M 11/045 | 126/200 |
| 7,281,382 B2 | 10/2007 | Plimpton et al. | | |
| 7,375,314 B2 | 5/2008 | Karst | | |
| 7,456,412 B2 | 11/2008 | Cole et al. | | |
| 7,710,280 B2 | 5/2010 | McLellan | | |
| 7,777,977 B2 | 8/2010 | Chase et al. | | |
| 7,987,712 B2 | 8/2011 | Myhre et al. | | |
| 8,153,952 B2 | 4/2012 | Haffner | | |
| 9,005,764 B2 * | 4/2015 | Yokoyama | C03C 17/04 | 428/220 |
| 2002/0192403 A1 * | 12/2002 | Hanna | C03C 27/044 | 428/34 |
| 2003/0076610 A1 * | 4/2003 | Anderson | F23M 11/042 | 359/892 |
| 2005/0268567 A1 * | 12/2005 | Devine | H01L 21/6719 | 52/204.5 |
| 2010/0265492 A1 | 10/2010 | Schroeder et al. | | |
| 2010/0313798 A1 * | 12/2010 | Murray | F23B 60/02 | 110/267 |
| 2012/0216568 A1 | 8/2012 | Fisher, Jr. et al. | | |
| 2012/0304585 A1 * | 12/2012 | Coatwala | E06B 3/5892 | 52/656.2 |
| 2014/0124260 A1 * | 5/2014 | Blakemore | F23M 11/045 | 174/652 |

* cited by examiner

COUPLINGS FOR FLAME OBSERVATION DEVICES

CROSS-REFERENCE TO RELATED APPLICATION

This application claims the benefit of priority under 35 U.S.C. §119(e) to U.S. Provisional Application No. 61/889,934, filed Oct. 11, 2013, which is incorporated herein by reference in its entirety.

BACKGROUND OF THE INVENTION

1. Field of the Invention

The present disclosure relates to combustion monitoring, and more particularly to couplings for connecting combustion instruments to combustion devices such as boilers.

2. Description of Related Art

Safe and efficient operation of combustion devices such as boilers requires observation and monitoring of flame within a combustion space of the combustion device. This generally requires physically coupling the instrument to the device as well as optically coupling the instrument to the flames within the device such that a portion of radiation emitted by the flames reaches the instrument. The instrument analyzes radiation received through the optical coupling for monitoring combustion occurring within the space, such as for flame presence, combustion stability and efficiency, combustion products, and the like.

Combustion instruments can be relatively intolerant of high temperature and pressure, being susceptible to performance degradation or damage if exposed to high pressures or temperatures. Since combustion devices can run at extremely high temperatures and pressures, and increasingly demanding efficiency and emissions requirements give rise to increasingly sophisticated monitoring instruments, coupling such instruments presents a continuing challenge.

Conventional instrument couplings and coupling methods have generally been considered satisfactory for their intended purpose. However, there is a need in the art for couplings that allow for safe coupling of instruments to combustion devices that operate at very high temperatures and pressures. There also remains a need for coupling devices and methods that are easy to make and use. The present disclosure provides a solution for these needs.

SUMMARY OF THE INVENTION

The subject disclosure is directed to a new and useful window for viewing combustion. The window includes a window body defining an interior surface, an opposed exterior surface, and a tapered seal surface spanning between the interior and exterior surfaces. The interior surface is configured for facing a combustion space, the exterior surface is configured for facing an instrument space, and the tapered seal surface is configured for separating the instrument space from the combustion space. The seal surface of the window body is tapered from the interior to the exterior surface.

The seal surface can receive a load having an axial force component of equal magnitude to an opposing axial force associated with pressure applied to the interior surface. The seal surface can have a taper of less than about 45 degrees relative to a longitudinal axis defined between the interior and exterior surfaces of the window body. For example, the window body taper can be between 35 degrees and 40 degrees. The window can be transmissive to radiation having wavelengths from 280 nm to 1200 nm.

A coupling for connecting a combustion space to an instrument space is also provided. The coupling includes a union body and a window as described above. A bore is defined extending through the union body having interior and exterior segments and with a tapered segment separating the interior segment from the exterior segment of the bore. The window is seated within the tapered segment of the bore for hermetically sealing the interior segment from the exterior segment and for optically coupling the combustion space to the instrument space. Either or both of the window body seal surface and bore tapered segment can include a sealant, such as graphite, so that the sealant is disposed between the union body and the window.

The interior segment of the bore can include a female threaded portion for coupling to the combustion space. The union body can also define a male threaded portion arranged radially outward of the exterior segment of the bore for coupling with the instrument space. The union body can define a circumferential rim extending about the exterior segment for coupling with the instrument space.

A flanged body can be radially received and axially fixed within the circumferential rim. It is contemplated that the flanged body can include an aperture with a female threaded portion outside an optical path defined therein and aligned with the bore of the union body for coupling with the instrument space. A locking member threaded to the male threaded portion of the union body can axially fix the flanged body against the union body.

In certain embodiments, the length of the tapered segment of the bore is greater than an axial thickness of the window body. The window can be disposed within the tapered segment of the bore with an interference fit. It is contemplated that the window and union body are combined such that force applied on the interior surface of the window body is less than an axial component of force applied on the seal surface of the window body. It is also contemplated that an axial component of force applied on the window seal surface can be greater than an oppositely directed force applied on the interior surface of the window body.

These and other features of the coupling devices and coupling methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods without undue experimentation, preferred embodiments thereof will be described in detail herein below with reference to certain figures, wherein.

DETAILED DESCRIPTION OF THE PREFERRED EMBODIMENTS

Figure 1:
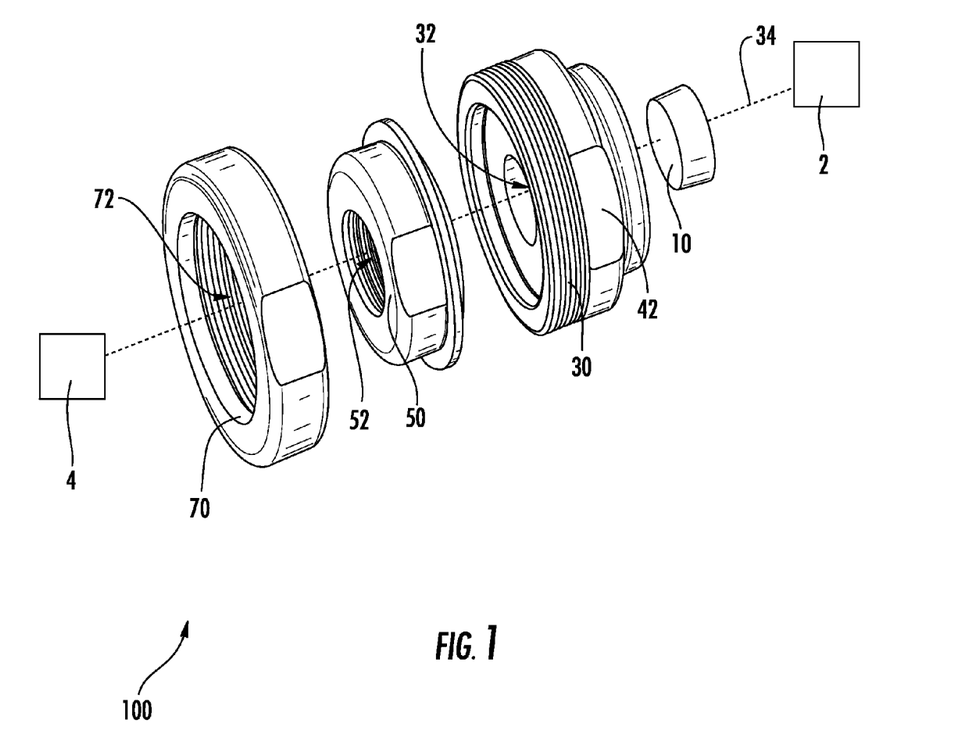
FIG. 1 is an exploded perspective view of an embodiment of a coupling in a disassembled configuration, showing a window, a union body, a flanged body, and a locking member.

Reference will now be made to the drawings wherein like reference numerals identify similar structural features or aspects of the subject disclosure. For purposes of explanation and illustration, and not limitation, a view of an exemplary embodiment of a coupling in accordance with the disclosure is shown in FIG. 1, and is designated generally by reference character 100. Other embodiments of couplings in accordance with the disclosure, or aspects thereof, are provided in FIGS. 2-6, as will be described. The devices and methods of the disclosure can be used for coupling instruments to combustion devices, such as for coupling flame scanners or flame detectors to turbine boilers for example.

Coupling 100 includes a window 10, a union body 30, a flanged body 50, and a locking member 70. Union body 30 has a bore 32 extending therethrough for optically coupling a combustion space 2 to an instrument space 4. Union body 30 is also configured and adapted for seating window 10 therein. Combustion space 2 and instruments space 4 are shown schematically in FIG. 1, however these spaces can represent a combustion device and a space with optical or flame sensing instruments, respectively for example.

Bore 32 defines a portion of an optical path through union body 30 along an optical axis 34 extending therethrough. Flanged body 50 has an aperture 52 that cooperates with bore 32 to form the optical path between combustion space 2 and instrument space 4. Locking member 70 has an aperture 72 configured and adapted to axially seat against and circumferentially surround flanged body 50. Union body 30, flanged body 50 and locking member 70 can be constructed from a corrosion resistant material, such as type 316 stainless steel for example. As will be appreciated by those skilled in the art, combustion space 2 can optically couple and mechanically connect to coupling 100 directly or through an intermediary device such as a sight pipe. Instrument space 4 can optionally optically couple and mechanically connect to coupling 100 through an intermediary device, such as a fiber optic waveguide for example. Coupling 100 can also optically couple and mechanically connect to either or both of combustion space 2 and instrument space 4 directly such as with conventional threaded fittings and the like.

Figure 2A:
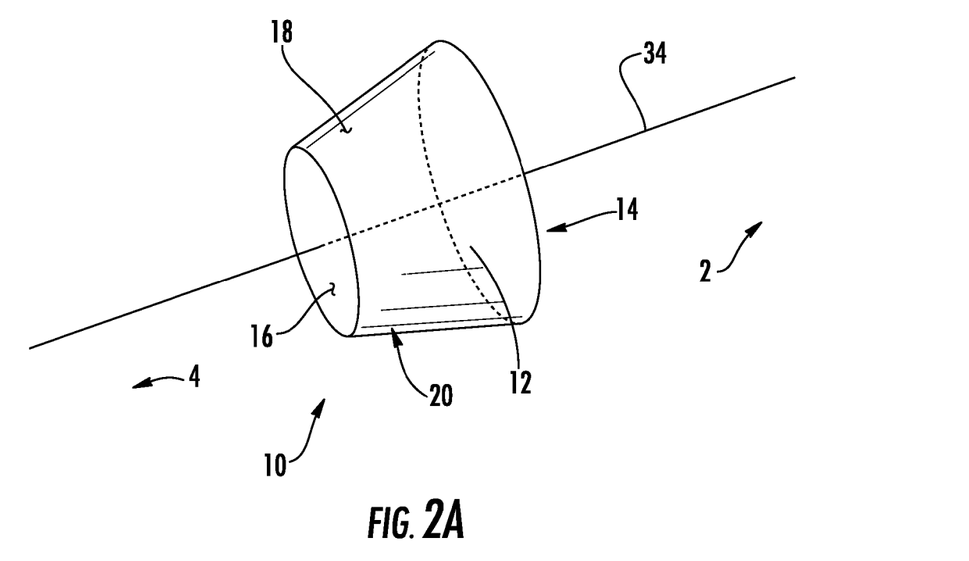
FIGS. 2A and 2B are perspective and side elevation views of the window of FIG. 1, showing the window body geometry.
Figure 2B:
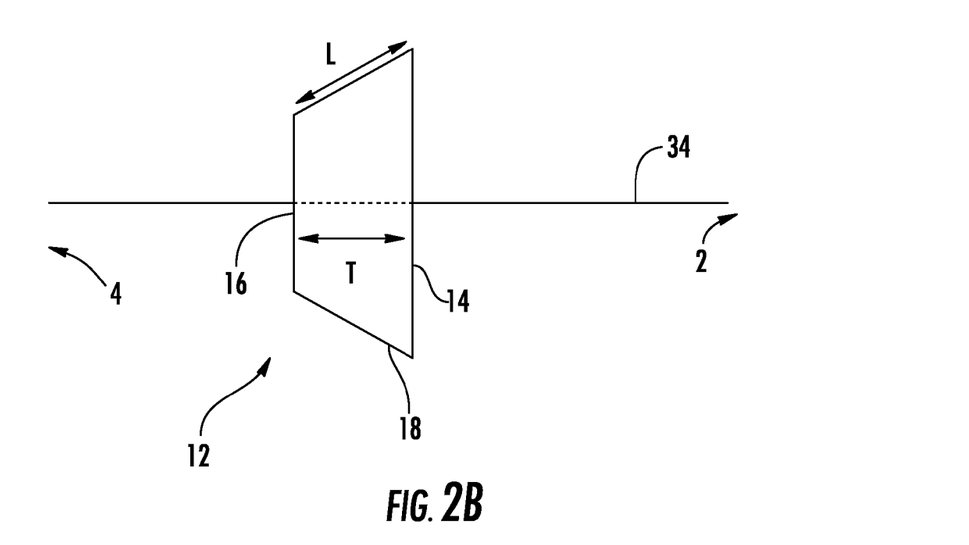

With reference to FIG. 2A and FIG. 2B, window 10 is shown. Window 10 is for viewing combustion in combustion space 2 and includes a window body 12. Window body 12 defines a radial body having an interior surface 14, an opposed external surface 16, and a tapered seal surface 18. Interior surface 14 faces combustion space 2, so that a portion of radiation emitted by flames within combustion space 2 is incident on interior surface 14. Exterior surface 16 faces instrument space 4 such that a portion of the radiation incident on interior surface 12 transits an axial thickness of window body 12 and is relayed by exterior surface 16 along the optical path to instrument space 4. Seal surface 18 tapers from interior surface 14 to exterior surface 16, such that a diameter of window body 12 at interior surface 14 is greater than the diameter of window body 12 at exterior surface 16.

With reference to FIG. 2B, seal surface 18 is obliquely oriented with respect to an axial thickness of window body 12 such that a line tangent to seal surface 18 intersects an optical axis 34 on a side of window 10 opposite combustion space 2 and towards instrument space 4. The tapered shape of window body 12 provides for hermetic sealing similar to that of a cork in the neck of a bottle.

Window body 12 is constructed of a material transparent to radiation of diagnostic interest to a combustion instrument. For example, window body 12 can be constructed of a material transmissive of ultraviolet (UV) radiation in the range of about 280 to about 1200 nanometers (nm). In certain embodiments, window body is transmissive to UV radiation in a band including 310 nm. Window 12 may be constructed from quartz, sapphire or fused silica for example.

With further reference to FIG. 2B, window body 12 has a thickness T along its axis. Seal surface 18 defines a profile having a length L. Length L is greater than thickness T and is oriented obliquely with respect to optical axis 34. In use seal surface 18 hermetically separates instrument space 4 from combustion space 2. Seal surface 18 can include a sealant 20 (shown in FIG. 2A) disposed over at least a portion of seal surface 18. This facilitates installing window 10 in union body 30, allowing window body 12 to seat axially in a narrower portion of bore 32 (shown in FIG. 6). Sealant 20 also occupies and occludes fissures proximate to seal surface 18 that otherwise could provide a pneumatic conduit about the periphery of window 10. Without wishing to be bound by a particular theory, it is believed that high pressure on interior surface 14, e.g. above ambient pressure opposing exterior surface 16, drives sealant 20 into fissures and clearances between window 10 and bore 32. Sealant 20 collects within the fissures and clearances in sufficient quantity and constitution to occlude channels that otherwise may exist between interior and exterior surfaces 14 and 16 and across seal surface 18. Heating of window body 12 facilitates the flow of sealant 20 into such fissures, such as through a thermal cycling process, conforming the sealant material into fissure plugs. Sealant 20 can be graphite for example.

Figure 3:
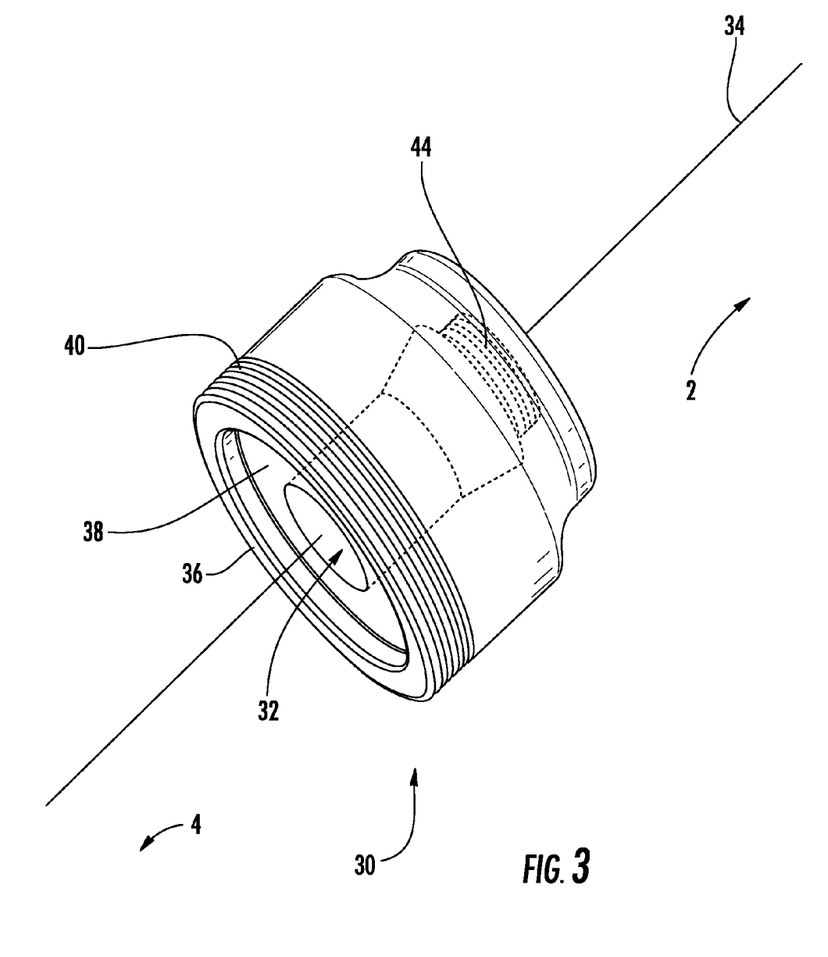
FIG. 3 is a perspective view of the union body of FIG. 1, showing features of the union body and bore therethrough.

With reference to FIG. 3, union body 30 is shown. Union body 30 defines a bore 32 extending therethrough and along optical axis 34. Bore 32 defines a portion of the optical path extending along optical axis 34 for coupling combustion space 2 with instrument space 4. On an exterior or instrument space 4 facing end, union body 30 defines a circumferential rim 36 with an axial wall height, a mate face surface 38, and a male threaded portion 40. Rim 36 is configured and adapted for radially capturing a flange 56 of a flanged body 50 (shown in FIG. 4) such that a bore 52 of flanged body 50 aligns with bore 32 of union body 30 along optical axis 34. Mate face surface 38 is substantially orthogonal with respect to optical axis 34, and is configured and adapted to receive seat 58 of flanged body 50 (shown in FIG. 4) to restrict its movement toward combustion space 2 along optical axis 34. Male threaded portion 40 is configured and adapted to threadably receive locking member 70 (shown in FIG. 5) such that flanged body 50 is axially fixed between union body 30 and locking member 70.

Union body 30 defines a female threaded portion 44 on an end facing combustion space 2. Female threaded portion 44 is configured and adapted to couple to a fitting or combustion device. Tool engagement surfaces 42 (shown in FIG. 1) defined by union body 30 along its midsection (only one of which is shown in FIG. 3 for purposes of clarity) cooperate with female threaded portion 44 to allow for mechanically coupling union body 30 to a combustion device defining combustion space 2.

Figure 4:
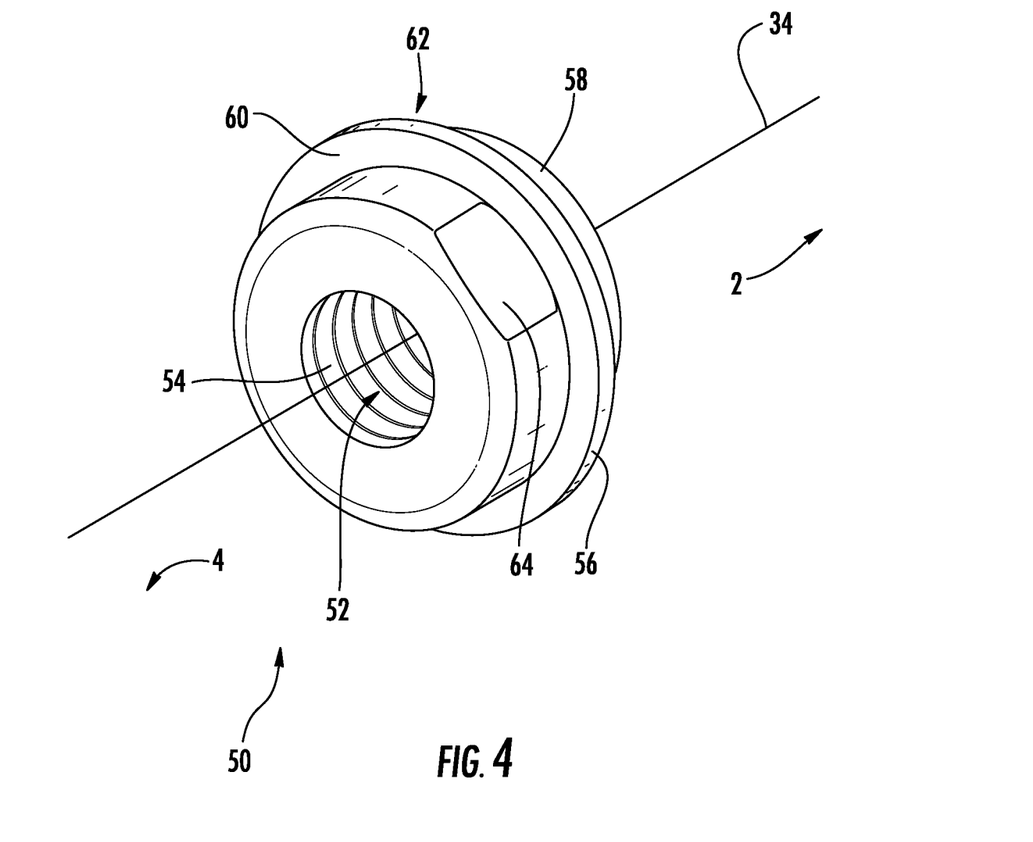
FIG. 4 is a perspective view of the flanged body of FIG. 1, showing features of the flanged body and aperture therethrough.

With reference to FIG. 4, flanged body 50 is shown. Flanged body 50 includes a bore 52 with a female threaded portion 54, a flange 56, and a seat 58. Bore 52 forms a portion of the optical path coupling combustion space 2 with instrument space 4. Bore 52 is coaxial with optical axis 34, providing for alignment of bore 52 with bore 32 of union body 30 along optical axis 34. Female threaded portion 54 circumferentially surrounds bore 52 radially along an optical path therethrough, and is configured and adapted to couple to an instrument such as a flame detector for example. Flange 56 extends radially outward from and circumferentially surrounds flanged body 50. Flange 56 defines a first surface 60 and an opposed second surface 62, first surface 60 facing instrument space 4 and second surface 62 facing combustion space 2. Flange 56 is configured and adapted for axial capture between locking member 70 and an opposed surface of rim 36 of union body 30. Seat 58 is also configured and adapted for radial capture against mate face surface 38 within rim 36 of union body 30. Seat 58 extends axially along a length corresponding to an axial depth of rim 36 of union body 30. Flanged body 50 also includes a plurality of tool engagement surfaces 64 (only one of which is shown in FIG. 4 for purposes of clarity). Tool engagement surfaces 64 allow for a tool, e.g. a pipe wrench, to independently rotate flanged body 50 for threadably engaging a coupling or instrument within female threaded portion 54 by rotating flanged body 50 using the tool.

Figure 5:
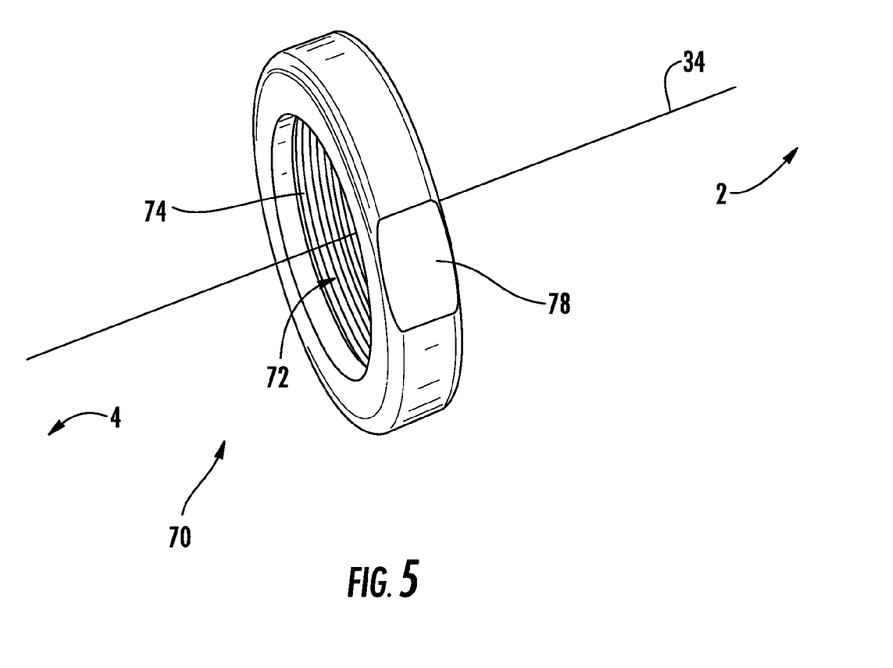
FIG. 5 is a perspective view of the locking member of FIG. 1, showing features of the locking member and aperture extending therethrough.

With reference to FIG. 5, locking member 70 is shown. Locking member 70 includes an aperture 72, a female threaded portion 74, a flange engagement surface 76 (shown in FIG. 6), and tool engagement surfaces 78 (only one of which is shown in FIG. 5 for purposes of clarity). Aperture 72 is aligned with optical axis 34. Female threaded portion 74 is configured and adapted to threadably couple with male threaded portion 40 of union body 30 for purposes of axially capturing flanged body 50 therebetween, such as by being torqued to a predetermined value for example. Flange engagement surface 76 corresponds to first surface 60 such that when locking member 70 is threadably attached to union body 30, flange engagement surface 76 couples axially with first surface 60 of flanged body 50.

Figure 6:
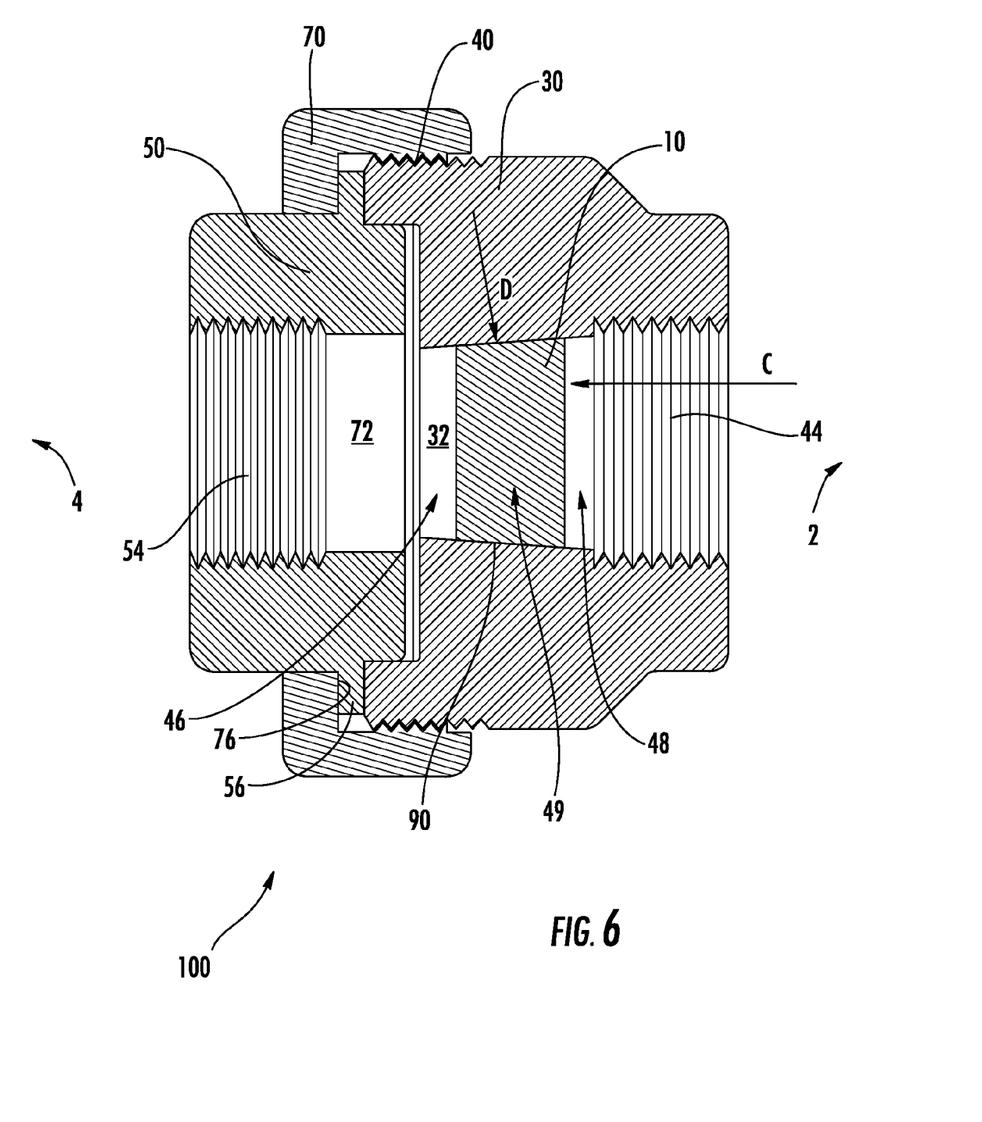
FIG. 6 is a cross-sectional view of the coupling of FIG. 1, showing the coupling in an assembled configuration.

With reference now to FIG. 6, coupling 100 is shown in an assembled configuration. Coupling assembly 100 includes window 10, union body 30, flanged body 50, and locking member 70 each as described above. Window 10 seats within bore 32. Bore 32 includes an exterior segment 46, an interior segment 48, and a tapered segment 49 extending between exterior segment 46 and interior segment 48 such that bore 32 uniformly tapers from a larger width at its interior segment, facing the combustion space, to a smaller opposing width at its exterior segment, facing instrument space 4. Window 10 seats within tapered segment 49 such that a force C applied on its interior surface 14 urges window 10 axially and toward instrument space 4 until a seal surface force D applied by union body 30 is of sufficient opposing axial force component to seat window body 12 in a fixed position within bore 32. As will be appreciated by those skilled in the art, lubricating interface 90 such as with sealant 20 allows for greater displacement of window body 12 toward the exterior segment of bore 32, in the direction of instrument space 4. Heating of union body 30 during the seating process also facilitates displacement as the corresponding bore diameter of union body 30 increases owing to the bore material having a greater coefficient of expansion than the window, resulting in an interference fit between the bore and window.

As will also be appreciated, while flanged body 50 is radially and axially captured to union body 30 by locking member 70, flanged body 50 is also free to rotate about optical axis 34, because female threaded portion 54 is configured to rotate freely about optical axis 34 in its captive position. This provides for physical and optical coupling an instrument to coupling 100 either directly or with an intermediate body, such as a wave guide for example, without disturbing union body 30 or its connection with combustion space 2.

Couplings as described herein allow instruments to be installed in close proximity to a combustion space without harm from exposure to high temperature and high pressure. For example, an instrument can be optically coupled to a combustion space to receive light at around the 310 nm wavelength from combustion occurring at pressures exceeding 1000 pounds per square inch at more than 1000° Fahrenheit safely, without risk to the measurement instrument or measurement information. Embodiments of the coupling can be installed between an instrument, such as flame scanning device, and a sight pipe coupled to a combustion space, such as a turbine boiler, for safe operation of the instrument. Embodiments of couplings described herein allow for safe removal and replacement of instruments without impact to the combustion space as the instruments can be removed and replaced by operation of the locking member and/or the flanged body. Instruments can also be coupled and uncoupled from the boiler without taking the boiler out of operation.

The devices and methods of the present disclosure, as described above and shown in the drawings, provide for coupling flame observation devices to high temperature and high pressure combustion devices. While the devices and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A coupling for connecting a combustion space to an instrument space, comprising:
    a union body with a bore extending therethrough, said bore comprising:
        an interior segment in proximity to the combustion space,
        an exterior segment in proximity to the instrument space, and
        a tapered segment extending between the interior segment and the exterior segment, the bore uniformly tapering from a larger width at the interior segment facing the combustion space to a smaller width at the exterior segment facing the instrument space; and
    a window for viewing combustion comprising a solid, tapered and transparent window body having an interior surface for facing the combustion space, an opposed exterior surface for facing the instrument space, and a seal surface spanning between interior and exterior surfaces, the seal surface tapering between the interior surface to the exterior surface, said window being seated within the tapered segment of the bore and hermetically sealing the interior segment from the exterior segment for optically coupling the combustion space with the instrument space,
        wherein the seal surface and a portion of the tapered segment abut one another in a lubricated interface disposed between the union body and the window.

2. A coupling as recited in claim 1, wherein the seal surface is configured and adapted to receive a load having an axial force component of equal magnitude to an opposing axial force associated with pressure applied to the interior surface.

3. A coupling as recited in claim 1, wherein the window is disposed about an optical axis and the seal surface has a taper between about 35 degrees and about 40 degrees relative to the optical axis extending between and through the interior and exterior surface of the window body.

4. A coupling as recited in claim 1, wherein the window is disposed about an optical axis and the seal surface has a taper of less than about 45 degrees relative to the optical axis defined extending between and through window body interior surface and exterior surface.

5. A coupling as recited in claim 1, wherein a sealant is disposed on the tapered seal surface.

6. A coupling as recited in claim 5, wherein the sealant is graphite.

7. A coupling as recited in claim 1, wherein the window body is transmissive to radiation having wavelengths from 280 nm to 1200 nm.

8. A coupling as recited in claim 1, wherein a length of the tapered segment of the bore is greater than an axial thickness of the window body.

9. A coupling as recited in claim 1, wherein the window is disposed within the tapered segment of the bore of the union body by an interference fit.

10. A coupling as recited in claim 1, wherein the window body and union body are configured so that force applied on the interior surface of the window is less than an axial component of force applied by the union body on the window seal surface.

11. A coupling as recited in claim 1, further comprising a sealant disposed between the bore and window seal surface.

12. A coupling as recited in claim 11, wherein the sealant is graphite.

13. A coupling as recited in claim 1, wherein the interior segment of the bore includes a female threaded portion for coupling to the combustion space.

14. A coupling as recited in claim 1, wherein the union body includes a male threaded portion radially outward of the exterior segment of the bore for coupling to the instrument space.

15. A coupling as recited in claim 14, wherein the union body defines a circumferential rim extending about the exterior segment for receiving a flanged body.

16. A coupling as recited in claim 15, further comprising a flanged body received within the circumferential rim of the union body.

17. A coupling as recited in claim 16, wherein the flanged body includes an aperture with a female threaded portion extending along an optical path defined by the aperture and aligned with the bore of the union body for coupling to the instrument space.

18. A coupling as recited in claim 17, further comprising a locking member adapted to threadably couple with the male threaded portion of the union body for axially fixing the flanged body between the locking member and the union body.

19. A coupling as recited in claim 18, wherein the locking member has an aperture aligned with the bore of the union body, and wherein the locking member circumferentially surrounds the flanged body.

* * * * *